(12) United States Patent
Dubief et al.

(10) Patent No.: US 6,369,117 B1
(45) Date of Patent: Apr. 9, 2002

(54) THICKENED AQUEOUS COMPOSITION AND USE

(75) Inventors: Claude Dubief, Chesnay; Christine Dupuis, Paris, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/341,518

(22) PCT Filed: Dec. 31, 1997

(86) PCT No.: PCT/FR97/02473

§ 371 Date: Oct. 12, 1999

§ 102(e) Date: Oct. 12, 1999

(87) PCT Pub. No.: WO98/31751

PCT Pub. Date: Jul. 23, 1998

(30) Foreign Application Priority Data

Jan. 14, 1997 (FR) .............................. 97 00294

(51) Int. Cl.[7] .............................. A61K 7/06; A61K 7/11; B01F 17/54; C08J 3/07; C08L 83/12

(52) U.S. Cl. .................. 516/55; 424/70.12; 424/70.16; 424/70.2; 514/944; 516/104; 516/105; 516/903; 526/932

(58) Field of Search ....................... 516/55, 104, 105, 516/903; 526/932; 424/70.16, 70.2, 70.12; 514/944

(56) References Cited

U.S. PATENT DOCUMENTS

| | | | |
|---|---|---|---|
| 4,384,096 A | 5/1983 | Sonnabend | 526/313 |
| 4,421,902 A | 12/1983 | Chang et al. | 526/317 |
| 4,423,199 A | 12/1983 | Chang et al. | 526/307.6 |
| 4,432,881 A * | 2/1984 | Evani | 516/104 X |
| 4,663,385 A | 5/1987 | Chang et al. | 524/523 |
| 5,059,414 A * | 10/1991 | Dallal et al. | 424/70.2 |
| 5,070,171 A | 12/1991 | O'Lenick, Jr. | 528/33 |
| 5,091,493 A | 2/1992 | O'Lenick, Jr. et al. | 528/30 |
| 5,093,452 A | 3/1992 | O'Lenick, Jr. | 528/25 |
| 5,143,724 A * | 9/1992 | Leshchiner et al. | 514/944 X |
| 5,149,765 A | 9/1992 | O'Lenick, Jr. | 528/25 |
| 5,330,758 A | 7/1994 | Hansenne-Richoux et al. | 424/450 |
| 5,417,965 A * | 5/1995 | Janchitraponvej et al. | 424/70.16 X |
| 5,433,890 A * | 7/1995 | Meyer et al. | 516/55 X |
| 5,443,760 A * | 8/1995 | Kasprzak | 516/55 X |
| 5,536,493 A | 7/1996 | Dubief | 424/70.13 |
| 5,656,257 A * | 8/1997 | Fealy et al. | 424/70.16 X |

FOREIGN PATENT DOCUMENTS

| | | |
|---|---|---|
| EP | 0 281 360 | 9/1988 |
| EP | 0 412 706 | 2/1991 |
| EP | 0 426 520 | 5/1991 |
| EP | 0 492 657 | 7/1992 |
| FR | 2 709 955 | 3/1995 |
| FR | 2 739 282 | 4/1997 |
| FR | 2 739 283 | 4/1997 |

OTHER PUBLICATIONS

Benoit Magny, "Polyélectrolytes associatifs: méthodes de synthèse comportement en milieu dilué et semi–dilué", Double Laison—Physique et Chimie des Peintures et Adhésifs, No. 451, Sep. 1993, pp. 52–55.

G. Shay, "A new class of alkali–swellable associative thickeners", Surface Coatings International, JOCCA, vol. 76, No. 11, Nov. 1993, pp. 446–453.

J.W. Goodwin et al., "The Rheological Properties of a Hydrophobically Modified Cellulose", Advances in Chemistry Series 223, 1987, pp. 365–378.

English language Derwent Abstract of FR 2 709 955, (1995).
English language Derwent Abstract of FR 2 739 282, (1997).
English language Derwent Abstract of FR 2 739 283, (1997).

* cited by examiner

Primary Examiner—Richard D. Lovering
(74) Attorney, Agent, or Firm—Finnegan, Henderson, Farabow, Garrett & Dunner, L.L.P.

(57) ABSTRACT

Compositions comprising, in an aqueous phase, at least one amphiphilic polymer comprising at least one fatty chain and hydrophilic units, and at least one polyoxyalkylene, and optionally comprising a thickening system for use in particular in cosmetics.

15 Claims, No Drawings

THICKENED AQUEOUS COMPOSITION AND USE

This is the U.S. National Phase application, filed under 35 U.S.C. §371, of international application PCT/FR97/02473 filed Dec. 31, 1997.

The present invention relates to an aqueous composition comprising a new thickening system, as well as to the use of this new thickening system in an aqueous composition which can be used in particular in the cosmetic field.

It is known to use, as aqueous-media thickening agent, water-soluble or water-dispersible polymers, and in particular optionally cross-linked polymers. The thickening is then caused by the entanglement of the polymer chains, the said amphiphilic polymers preferably having a long chain length and a high molecular weight.

It is also known to use, as aqueous-media thickener, hydrophilic polymers containing hydrophobic groups which exist in the form of randomly distributed side groups, grafts and/or blocks. These amphiphilic polymers make it possible to obtain substantial thickening of the medium even when they are used in a small quantity. The thickening is generated by the formation of aggregates between the hydrophobic groups of the amphiphilic polymer, these aggregates constituting physical cross-linking points between the macromolecular chains. However, it has been observed that the presence of hydrophilic polymers with hydrophobic groups, even in a small quantity, in compositions, especially cosmetic compositions, could modify in an undesirable manner the cosmetic properties of the said compositions, for example the properties of feel or spreading.

On the other hand, it is also known to prepare hair compositions in the form of a gel comprising polymers with hydrophobic units combined with surfactants; the gel is then formed by virtue of the formation of mixed micelles. However, it has been observed that the texture obtained was often brittle, which made the composition hardly prehensible; furthermore, the presence of an excess of surfactant could lead to certain disadvantages in the field of leave-in compositions.

The patent application EP 0,412,706 describes a particular carrier for cosmetic compositions which is intended to produce a rheology resembling that of a gel. This vehicle comprises a thickening polymer and a surfactant. The thickening polymer is a nonionic polymer whose backbone is soluble in water and whose grafts are hydrophobic. It may be for example a cellulose ether which has been made hydrophobic. The surfactant may be a copolyol silicone.

However, this vehicle system limits the range of viscosities of the compositions obtained and does not make it possible to obtain gels which are clear in appearance. Moreover, the cosmetic properties obtained with this carrier remain inadequate, especially if the polymer concentration is increased in order to increase the thickening.

Thus, the need remains for a thickening system which makes it possible to thicken or even gel, in a suitable manner, in a very wide range of viscosities, a composition comprising an aqueous phase, without influencing the cosmetic properties of the said compositions.

The aim of the present invention is to provide such a thickening system which makes it possible, furthermore, to obtain an adequate thickening using a very small quantity of thickening amphiphilic polymer.

A subject of the present invention is therefore an aqueous composition comprising the combination of an amphiphilic polymer which contains at least one fatty chain and hydrophilic units, and of a polyoxyalkylenated silicone, the amphiphilic polymer not being a cellulose ether which has been made hydrophobic.

Another subject of the invention is the use of the combination of a polyoxyalkylenated silicone and of an amphiphilic polymer which contains at least one fatty chain and hydrophilic units, as thickening agent, in particular in a composition comprising an aqueous phase, the amphiphilic polymer not being a cellulose ether which has been made hydrophobic.

Finally, another subject of the invention is the use of a polyoxyalkylenated silicone for enhancing the thickening power of an amphiphilic polymer which contains at least one fatty chain and hydrophilic units in a composition comprising an aqueous phase, the amphiphilic polymer not being a cellulose ether which has been made hydrophobic.

It has therefore been observed that such a combination made it possible to obtain, in an aqueous medium, a high increase in the viscosity which may extend up to complete gelling of the medium.

It is therefore possible to arrive at the same degree of thickening, or even of gelling, using smaller quantities of amphiphilic polymer, while preserving good cosmetic properties. It should be noted that depending on the amphiphilic polymer and the quantities in which it is used in the presence of silicone, its use in the absence of polyoxyalkylenated silicone does not necessarily make it possible to obtain thickening of the medium.

The polyoxyalkylenated silicone/amphiphilic polymer interaction therefore makes it possible to very easily adjust the degree of viscosity of the medium simply by mixing, in proportions which can be adjusted at will.

Moreover, the cosmetic, and in particular hair, composition obtained is easy to spread, exhibits a better prehension, as well as a better removal on rinsing.

Without being held to this explanation, it is possible to consider that, within the framework of the invention, the increase in the viscosity of the medium results from a physical crosslinking between the polymer chains and the silicone, the said crosslinking being reversible and involving combinations or interactions of the hydrophobic type between, on the one hand, the hydrophobic groups of the amphiphilic polymer and, on the other hand, the hydrophobic sites of the silicone.

These hydrophobic-type interactions then lead to the gelling network.

The polymers capable of being used in the present invention are amphiphilic polymers which contain at least one fatty chain, therefore a hydrophobic part, and hydrophilic units, therefore a hydrophilic part.

The hydrophobic part may be in a small number compared with the rest of the polymeric chain, and may be situated on the side of the chain and may be distributed randomly (random copolymers) or may be distributed in the form of blocks or grafts (block copolymers).

It is possible to use water-soluble or water-dispersible polymers. Preferably, the amphiphilic polymers which are used according to the invention are not crosslinked.

The amphiphilic polymers may be of any chemical nature; it is thus possible to choose natural, optionally modified, polymers; radicular, in particular vinyl or acrylic, polymers; polycondensates; and mixtures thereof.

They may be ionic or nonionic, and are preferably anionic or nonionic.

The expression "hydrophobic chain" should be understood according to the invention to mean a linear or branched hydrocarbon group having from 8 to 28 carbon atoms capable of comprising heteroatoms such as oxygen, nitrogen or sulphur.

There may be mentioned in particular, among the amphiphilic polymers according to the invention, the polymers derived from the following natural polymers:

quaternized cationic celluloses modified by groups containing at least one fatty chain such as alkyl, arylalkyl or alkylaryl groups or mixtures thereof where the alkyl groups are preferably $C_8$–$C_{22}$, in particular quaternized alkylhydroxyethylcelluloses such as the products QUATRISOFT LM 200, QUATRISOFT LM-X 529-18-A, QUATRISOFT LM-X 529-18-B ($C_{12}$ alkyl) and QUATRISOFT LM-X 529-8 ($C_{18}$ alkyl) marketed by the company AMERCHOL and the products CRODACEL QM, CRODACEL QL ($C_{12}$ alkyl) and CRODACEL QS ($C_{18}$ alkyl) marketed by the company CRODA;

galactomannans possessing hydrophobic substituents, and in particular hydrophobic substituted guar gums (in particular those described in EP281360) and the hydroxypropylguar gums modified by groups containing at least one fatty chain such as the product ESA-FLOR HM 22 ($C_{22}$ alkyl chain) marketed by the company LAMBERTI, the products MIRACARE XC95-3 ($C_{14}$ alkyl chain) and RE205-1 ($C_{20}$ alkyl chain) marketed by the company RHONE POULENC;

pullulons modified by hydrophobic groups, in particular cholesterol groups;

gelatins modified by hydrophobic groups, and in particular modified by $C_6$ to $C_{18}$ alkyl groups;

muccopolysaccharides such as those consisting of glycosaminoglycan and hyaluronic acid.

Among the polycondensates which are used according to the invention, there may be mentioned the associative polyurethanes which are nonionic block copolymers containing, in the chain, both hydrophilic blocks more often of a polyoxyethylene nature and hydrophobic blocks which may be aliphatic stretches alone and/or cycloaliphatic and/or aromatic stretches.

The resulting block copolymers may be of the triblock or multiblock type. The hydrophobic blocks may therefore be each end of the chain (triblock copolymers with a central polyoxyethylene block) or distributed both at the ends and in the chain (multiblock copolymers). They may also be in the form of grafts or of a star.

There may be mentioned the polymers described in the article by ZEYING MA, J. of Appl. Polymer Sci, vol. 49, 1509–27 (1993).

Among the commercially available polymers, there may be mentioned the products SER-AD FX1100 and SER-AD FX1035 marketed by the company HOLS.

Among the radicular amphiphilic polymers which are used according to the invention, there may be mentioned the anionic acrylic polymers, in aqueous dispersion, generally designated by the name HASE (hydrophobically modified alkalisoluble or swellable emulsion).

They are acrylic copolymers which exist in the form of dispersions in water at acidic pH and which become solubilized in water upon complete neutralization of the anionic groups, that is to say above pH 8.

These copolymers are generally terpolymers between a monomer carrying a carboxylic acid (acrylic, methacrylic acid) group, a relatively water-insoluble monomer of the $C_1$ to $C_4$ acrylate or methacrylate type, such as ethyl acrylate, and a third monomer carrying a hydrophobic group, which may be attached to the side of the main chain. This hydrophobic group may be a linear or branched $C_8$–$C_{22}$ alkyl group and/or a $C_8$–$C_{22}$ cycloalkyl group and/or an aryl group. The hydrophobic group may be attached to the main chain directly through a carbamate or urea, ether, ester or amide bond. It may also be attached to the main chain through a polyoxyethylenated block, itself attached to the chain by a carbamate, urea, ether, ester or amide bond. In the latter case, the side groups are generally small grafts with a hydrophilic and hydrophobic block and the aqueous-media thickening properties are better.

Such aqueous dispersions of amphiphilic polymer are in particular described in SHAY, (Surface Coatings International, 1993 (11) 446–453), and in U.S. Pat. Nos. 4,421,902, 4,423,199 and 4,663,385 to Rohm and Haas, and U.S. Pat. No. 4,384,096 to Dow Corning.

The products Acusol 823 and Acrysol 25 or 22 marketed by the company Rohm & Haas may also be mentioned.

Among the free-radical polymers according to the invention, there may also be mentioned:

the acrylic acid or methacrylic acid copolymers with Nalkylacrylamides, and in particular the acrylic acid/Nalkylacrylamide copolymers having a $C_1$ to $C_{20}$ alkyl group such as those described in the article MAGNY et al., Double Liaison, 451, p 52–55 (1993). They may be obtained by direct copolymerization or by subsequent amidation of the acrylic acid chain. Depending on the procedure used, the hydrophobic alkyl groups may be randomly distributed (amidation in homogeneous organic solution) or in block form (amidation in aqueous medium where the amine initially forms aggregates of the micellar type), the copolymers between a monomer having a carboxylic acid group, for example methacrylic acid, and methacrylates of esters or amides carrying cycloaliphatic or aromatic hydrophobic groups, such as isobornyl or adamantyl groups, the copolymers with perfluorinated monomers, in particular the copolymers with (perfluorohexyl methacrylate; copolymers between a monomer carrying a sulphonic acid group (in particular a 2-acrylamido-2-methylpropane sulphonic acid, styrenesulphonic acid) and an alkyl (meth)acrylamide possessing at least 8 carbons, the nonionic acrylic copolymers, and in particular copolymers of the acrylamide/N-alkylacrylamide type, such as those described in GOODWIN et al., Polymer in Aqueous Media=Performance Through Association, (J. E. Glassed) Adv. Chem. Ser. 223; Am. Chem. Soc., Washington D.C., p 365 (1989).

the polymers of (methacrylic acid which are modified by groups carrying at least one fatty chain or copolymers of (methacrylic acid and monomers containing at least one fatty chain; these monomers are chosen from the hydrophobic monomers having a fatty chain, the amphiphilic monomers containing a hydrophobic part having a fatty chain and a hydrophilic part or alternatively mixtures thereof; there may be mentioned by way of example:

the (meth)acrylic acid/ethyl acrylate/$C_8$–$C_{22}$ alkyl acrylate copolymers such as the product ACUSOL 823 marketed by the company ROHM & HAAS and the product IMPERON-R marketed by the company HOECHST;

the acrylic acid/lauryl (meth)acrylate copolymers such as the products COATEX SX marketed by the company COATEX;

the (meth)acrylic acid/$C_1$–$C_{22}$ alkyl acrylate polyethoxylated $C_1$–$C_{22}$ alkyl allyl ether copolymers in which at least one of the contains a $C_8$–$C_{22}$ alkyl chain such as the products RHEOVIS-CR, -CR3, -CR2 and CRX marketed by the company ALLIED COLLOIDS;

the methacrylic acid/ethyl acrylate/polyoxyethylenated lauryl acrylate terpolymers such as the product RHEO 2000 marketed by COATEX;

the methacrylic acid/ethyl acrylate/polyoxyethylenated stearyl methacrylate copolymers such as the products ACRYSOL 22, ACRYSOL25 and DW-1206A marketed by the company ROHM & HAAS;

the methacrylic acid/ethyl acrylate/polyoxyethylenated nonylphenol acrylate copolymers such as the product RHEO 3000 marketed by COATEX;

the acrylic acid/polyoxyethylenated stearyl monoitaconate copolymers or the acrylic acid/polyoxyethylenated cetyl monoitaconate copolymers such as the products 8069–72A and 8069–72B marketed by NATIONAL STARCH;

the methacrylic acid/butyl acrylate/fatty chain-containing hydrophobic monomer copolymers such as the product 8069-146A marketed by NATIONAL STARCH;

the acrylic acid/$C_8$–$C_{20}$ alkyl acrylate terpolymers. Preferably $C_{15}$/polyethylene glycol acrylate (preferably having 20 to 30 mol of ethylene oxide) such as the product DAPRAL GE 202 marketed by the company AKZO;

the copolymers of (meth)acrylic acid/$C_1$–$C_{22}$ alkyl acrylate/amphiphilic monomer containing a $C_8$–$C_{22}$ hydrocarbon chain (for example alkyl or alkenyl) comprising urethane groups such as the product ADDITOL VXW 1312 marketed by HOECHST;

the acrylic polymers modified by hydrophobic groups having a fatty chain ($C_8$–$C_{22}$ hydrocarbon chain such as alkyl or alkenyl) such as the product CS-0406 marketed by ROHM & HAAS.

Among the amphiphilic polymers, there are preferred those chosen from the group consisting of:

the terpolymers of acrylic acid/$C_1$–$C_{18}$ alkyl acrylate/stearyl methacrylate polyoxyethylenated, for example, with the aid of 20 mol of ethylene oxide, such as the product marketed under the name "ACRYSOL ICS-IE®" by the company ROHM & HAAS, the (meth)acrylic acid/ethyl acrylate/$C_8$–$C_{22}$ alkyl acrylate terpolymers such as the product marketed under the name "IMPERON R" by the company HOECHST, the terpolymers of (meth)acrylic acid/$C_8$–$C_{22}$ alkyl acrylate/polyethoxylated $C_1$–$C_{22}$ alkyl allyl ether in which at least one of the monomers comprises a $C_8$–$C_{22}$ alkyl, such as the products marketed under the names "RHEOVIs-CR®, -CR$_2$®, -CR$_3$® and -CRX®" by the company ALLIED COLLOIDS, the (meth)acrylic acid/ethyl acrylate/polyoxyethylenated stearyl methacrylate terpolymers such as those marketed under the names "ACRYSOL 25®" and "DW-1206A®" by the company ROHM & HAAS.

Depending on their nature, the amphiphilic polymers according to the invention may be used in the form of aqueous solutions or in the form of aqueous dispersions.

A film-forming polymer or a non-film-forming polymer, or even a mixture of film-forming or non-film-forming polymer may equally well be used.

The compositions according to the invention comprise, in addition, necessarily at least one polyoxyalkylenated silicone.

According to the invention, polyoxyalkylenated silicone designates any silicone containing at least one oxyalkylenated group of the $(-C_xH_{2x}O)_a$ type in which x may vary from 2 to 6 and a is greater than or equal to 2.

Throughout the following or preceding text, silicone is intended to designate, in accordance with the general meaning, any organosilicon polymers or oligopolymers with a branched or crosslinked, linear or cyclic structure, of variable molecular weight, obtained by polymerization and/or polycondensation of suitably functionalized silanes, and essentially consisting of a repetition of main units in which the silicon atoms are linked to each other by oxygen atoms (siloxane bond ≡Si—O—Si≡), optionally substituted hydrocarbon radicals being directly linked via a carbon atom on the said silicon atoms. The most common hydrocarbon radicals are the alkyl, especially $C_1$–$C_{10}$, and in particular methyl, radicals, the fluoroalkyl radicals, the aryl, and in particular phenyl, radicals.

In accordance with the invention, the oxyalkylenated silicones are chosen from the compounds of general formulae (I), (II), (III), (IV) or (V):

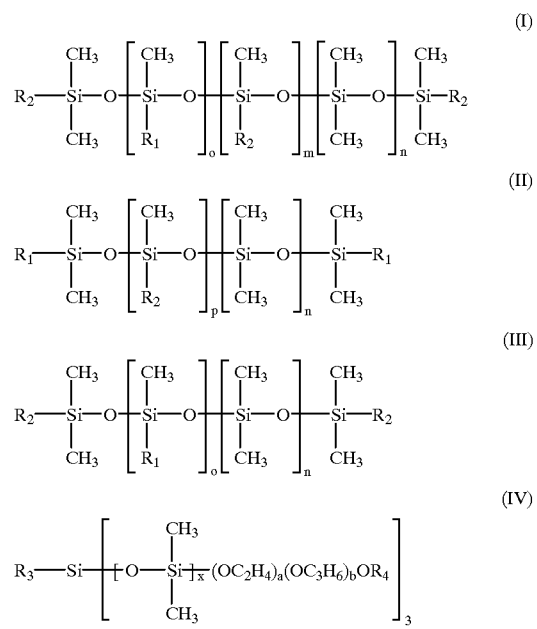

in which formulae (I), (II), (III) and (IV):

$R_1$, which is identical or different, represents a linear or branched $C_1$–$C_{30}$ alkyl or phenyl radical, $R_2$, which is identical or different, represents a radical $-C_cH_{2c}-O-(C_2H_4O)_a(C_3H_6O)_b-R_5$ or a radical $-C_cH_{2c}-O-(C_4H_8O)_a-R_5$, $R_3$, $R_4$, which are identical or different, designate a linear or branched $C_1$ to $C_{12}$ alkyl radical and preferably the methyl radical, $R_5$, which is identical or different, is chosen from a hydrogen atom, a linear or branched alkyl radical having 1 to 12 carbon atoms, a linear or branched alkoxy radical having 1 to 6 carbon atoms, a linear or branched acyl radical having 2 to 30 carbon atoms, a hydroxyl radical, a radical $-SO_3M$, a $C_1$–$C_6$ aminoalkoxy radical optionally substituted on the amine, a $C_2$–$C_6$ aminoacyl radical optionally substituted on the amine, a radical $-NHCH_2CH_2COOM$, a radical $-N(CH_2CH_2COOM)_2$, an aminoalkyl radical optionally substituted on the amine and on the alkyl chain, a $C_2$–$C_{30}$ carboxyacyl radical, a group optionally substituted with one or two substituted aminoalkyl radicals, a radical —CO(CH$_2$)$_d$COOM, a radical —COCHR$_7$(CH$_2$)$_d$COOM, a radical —NHCO(CH$_2$)$_d$OH, a radical —NH$_3$Y, a phosphate group, M, which is identical or different, designates a hydrogen atom, Na, K, Li, NH$_4$ or an organic amine, R$_7$ designates a hydrogen atom or a radical SO$_3$M, d varies from 1 to 10, m varies from 0 to 20, n varies from 0 to 500, o varies from 0 to 20, p varies from 1 to 50, a varies from 0 to 50, b varies from 0 to 50, a+b is greater than or equal to 2, c varies from 0 to 4, x varies from 1 to 100, Y represents a monovalent inorganic or organic anion such as a halide (chloride, bromide), sulphate, carboxylate (acetate, lactate, citrate), provided that when the silicone is of the formula (II) with R$_5$ designating hydrogen then n is greater than 12.

Such silicones are for example marketed by the company GOLDSCHMIDT under the tradenames ABIL WE 09, ABIL EM 90, ABIL B8852, ABIL B8851, ABIL B8843, ABIL B8842, by the company DOW CORNING under the names FLUID DC 190, DC 3225 C, Q2-5220, Q25354, Q2-5200, by the company RHONE POULENC under the names SILBIONE HUILE 70646, RHODORSIL HUILE 10634, by the company GENERAL ELECTRIC under the names SF1066, SF1188, by the company SWS SILICONES under the name SILICONE COPOLYMER F 754, by the company AMERCHOL under the name SILSOFT BEAUTY AID SL, by the company SHIN-ETSU under the name KF 351, by the company WACKER under the name BELSIL DMC 6038, by the company SILTECH under the names SILWAX WD-C, SILWAX WD-B, SILWAX WD-IS, SILWAX WSL, SILWAX DCA 100, SILTECH AMINE 65, by the company FANNING CORPORATION under the names FANCORSIL SLA, FANCORSIL LIM1, by the company PHOENIX under the name PECOSIL. These silicones are in particular described in U.S. Pat. Nos. 5,070,171, 5,149,765, 5,093,452 and 5,091,493.

Preferably, the polyoxyalkylenated silicones corresponding to the general formulae (II) or (III) are used. More particularly, these formulae comply with at least one, and preferably all, of the following conditions:

c is equal to 2 or 3.

R$_1$ designates the methyl radical.

R$_5$ represents a methyl radical, a C$_{12}$–C$_{22}$ acyl radical, a radical —CO(CH$_2$)$_d$COOM.

a varies from 2 to 25 and more particularly from 2 to 15.

b is equal to 0.

n varies from 0 to 100.

p varies from 1 to 20.

The polyoxyalkylenated silicones according to the invention may also be chosen from the silicones of the following formula (V):

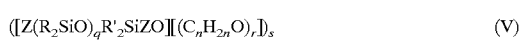
$$([Z(R_2SiO)_qR'_2SiZO][(C_nH_{2n}O)_r])_s \qquad (V)$$

in which formula (V):

R and R' which are identical or different, represent a monovalent hydrocarbon radical, n is an integer ranging from 2 to 4, q is a number greater than or equal to 4, preferably between 4 and 200 and still more particularly between 4 and 100.

r is a number greater than or equal to 4, preferably between 4 and 200 and still more particularly between 5 and 100.

s is a number greater than or equal to 4, preferably between 4 and 1000 and still more particularly between 5 and 300.

Z represents a divalent organic group which is linked to the adjacent silicon atom by a carbon-silicon bond and to a polyoxyalkylene block by an oxygen atom, the average molecular weight of each siloxane block is between about 400 and about 10,000, that of each polyoxyalkylene block being between about 300 and about 10,000, the siloxane blocks represent from about 10% to about 95% by weight of the block copolymer, it being possible for the number-average molecular weight of the block copolymer to range from 2500 to 1,000,000 and preferably between 3000 and 200,000 and still more particularly between 6000 and 100,000.

R and R' are preferably chosen from the group comprising linear or branched alkyl radicals such as for example methyl, ethyl, propyl, butyl, pentyl, hexyl, octyl, decyl or dodecyl radicals, aryl radicals such as for example phenyl or naphthyl, aralkyl or alkylaryl radicals such as for example benzyl or phenylethyl, tolyl or xylyl radicals.

Z is preferably —R"—, —R"—CO—, —R"—NHCO—, —R"—NH—CO—NH—R'"—, —R"—OCONH—R'"—NHCO—, or R" is a linear or branched divalent C$_1$–C$_6$ alkylene group, such as for example ethylene, propylene or butylene, linear or branched, and R'" is a divalent alkylene group or a divalent arylene group such as —C$_6$H$_4$—, —C$_6$H$_4$—C$_6$H$_4$—, —C$_6$H$_4$—CH$_2$—C$_6$H$_4$—, —C$_6$H$_4$—C(CH$_3$)$_2$C$_6$H$_4$—.

Still more preferably, Z represents a divalent alkylene radical, more particularly the radical —C$_3$H$_6$— or the C$_4$H$_8$ radical, which are linear or branched.

The preparation of the block copolymers used within the framework of the present invention is described in European Application EP 0 492 657 A1, whose teaching is incorporated into the present description.

Such products are, for example, marketed under the name SILICONE FLUID FZ-2172 by the company OSI.

The silicones according to the invention may be provided in the form of aqueous solutions or optionally in the form of aqueous dispersions or emulsions.

The combination according to the invention may in particular be used to thicken or even gel aqueous media so as to obtain, for example, aqueous gels.

It may optionally be used in the context of the thickening of emulsions, in particular for emulsions free of surfactants, or for the thickening of aqueous dispersions.

It is thus possible to envisage applications in particular in the fields of cosmetics, dermatology or hygiene for the thickening in particular of care or cleansing gel for the skin or the hair, hairstyling gel, anti-sun gel, make-up gel and dentibuccal gel or for the thickening of emulsions and in particular of oil-in-water emulsions, for example in care, cleansing or make-up creams for the skin or the hair, anti-sun or even hair creams.

Preferably, the composition according to the invention comprises less than 5% by weight of surfactant.

The quantities of oxyalkylenated silicone and of amphiphilic polymer to be added to an aqueous medium may also be determined by a person skilled in the art on the basis of their general knowledge. It is also possible in particular to envisage a composition comprising 0.1 to 15% by weight of amphiphilic polymer, preferably from 0.2 to 10% by weight relative to the total weight of the composition. The quantity of silicone may be from 0.005% to 15% by weight relative to the total weight of the composition. Preferably, the silicones are used in a quantity such that a silicone/amphiphilic polymer weight ratio of between 0.1 and 10 is obtained.

It is thus possible to obtain a thickening composition, having a viscosity of between 200 and 30,000 cp (mPa.s), comprising a very small quantity of thickening agents, which may be of the order of 0.8 to 3% by weight for example.

Depending on the application envisaged, the composition may comprise the usual constituents for this type of composition.

There may be mentioned any customary additive used in the field considered, such as pigments, fillers and/or pearlescent agents, antioxidants, perfumes, preservatives, cosmetic or pharmaceutical active agents, moisturizers, vitamins, essential fatty acids, sunscreens, surfactants, agents for tanning without sun.

Of course the person skilled in the art will be careful to choose this or these optional additional compounds, and/or their quantity, such that the advantageous properties of the composition according to the invention are not, or not substantially, altered by the addition envisaged.

The invention is illustrated in greater detail in the following examples.

EXAMPLE 1

The viscosity at 25° C. of an aqueous composition comprising 1% by weight of polymer active material and 0.1% or 0.5% by weight of silicone active material (pH 7 with 2-amino-2-methyl-1-propanol) is measured.

The following results are obtained:

| Polymer | Silicone | Viscosity |
|---------|----------|-----------|
| 1% Acrysol ICS | — | 1300 cps |
| 1% Acrysol ICS | 0.1% Fancorsil SLA | 1650 cps |
| 1% Acrysol ICS | 0.1% Silwax WDIS | 1700 cps |
| 1% Acrysol ICS | 0.1% Fancorsil LIM-1 | 2400 cps |
| 1% Acrysol ICS | 0.5% Fancorsil LIM- | 4300 cps |
| 1% Acrysol ICS | 0.1% Silwet L 77 | 2700 cps |
| 1% Acrysol ICS | 0.1% Silphos A 100 | 1750 cps |
| 1% Acrysol ICS | 0.5% Silphos A 100 | 2400 cps |
| 1% Acrysol ICS | 0.1% Silicone sulphate | 2080 cps |

The compounds used are the following:
Acrysol ISC marketed by Rohm & Haas: Terpolymer of acrylic acid/$C_1$–$C_{18}$ alkyl acrylate/polyoxyethylenated stearyl methacrylate containing 20 mol of ethylene oxide
Fancorsil SLA marketed by Fanning Corporation: Polyoxyethylenated polydimethylsiloxane containing adipate groups
Silwax WD-IS marketed by Siltech: Polyoxyethylenated polydimethylsiloxane containing stearate groups
Fancorsil LIM-1 marketed by Fanning Corporation: Polyoxyethylenated polydimethylsiloxane containing eicosanoate groups
Silwet L 77 marketed by OSI: Polyoxyethylenated heptamethyltrisiloxane containing 8 mol of ethylene oxide
Silphos A 100 marketed by Siltech: Polyoxyethylenated polydimethylsiloxane containing phosphate groups
Silicone sulphate marketed by Siltech: Polyoxyethylenated polydimethylsiloxane containing sulphate groups It is therefore observed that the addition of a silicone to an amphiphilic polymer makes it possible to enhance the thickening power of the said amphiphilic polymer whereas the silicone used alone gives no viscosity.

Furthermore, the composition obtained has sufficient viscosity, while comprising a small quantity of thickener.

These compositions have a nonbrittle melting texture.

EXAMPLE 2

A hairstyling gel having the following composition is prepared:

| | | |
|---|---|---|
| Methacrylic acid/ethyl acrylate/ polyoxyethylenated stearyl methacrylate terpolymer (ACRYSOL 22 from Rohm & Haas) | | 2 g |
| SILWAX WD IS | | 0.3 g |
| 2-amino-2-methylpropanol- | qs | pH 7.5 |
| demineralized water | qs | 100 g |

EXAMPLE 3

A hairstyling gel having the following composition is prepared:

| | | |
|---|---|---|
| ACRYSOL 22 | | 1 g |
| SILPHOS A 100 | | 0.5 g |
| 2-amino-2-methyl-1-propanol | qs | pH 7.5 |
| demineralized water | qs | 100 g |

EXAMPLE 4

A hairstyling gel having the following composition is prepared:

| | | |
|---|---|---|
| Methacrylic acid/C8-C22 alkyl acrylate/C1-C22 alkyl alkyl ether copolymer (RHEOVIS CR from Allied Colloid) | | 4 g |
| SI LWET L77 | | 0.4 g |
| 2-amino-2-methyl-1-propanol | qs | pH 7 |
| ethanol | | 6.8 g |
| demineralized water | qs | 100 g |

EXAMPLE 5

Compositions in accordance with the invention comprising, as amphiphilic polymer, Acrysol 22 are compared with compositions in accordance with the prior art comprising Natrosol Plus. A copolyol silicone is used as polyoxyalkylenated silicone. The viscosity as well as the cosmetic response which are obtained for either of the formulations is studied.

| | A | B | C | D | E | F |
|---|---|---|---|---|---|---|
| Acrysol 22 | 1 | | 1 | | 1 | |
| AMP | 0.35 | | 0.35 | | 0.35 | |

-continued

|  | A | B | C | D | E | F |
|---|---|---|---|---|---|---|
| Natrosol Plus |  | 1 |  | 1 |  | 1 |
| Silwet L77 |  |  | 0.1 | 0.1 |  |  |
| Fancorsil LIM |  |  |  |  | 0.1 | 0.1 |
| Water qs (g) | 100 | 100 | 100 | 100 | 100 | 100 |

Viscosity energy

|  | A | B | C | D | E | F |
|---|---|---|---|---|---|---|
| Viscosity (cps) | 1060 | 160 | 3400 | 224 | 2030 | 216 |

Compositions C and E are markedly superior to A. Compositions D and F are equivalent to B.

Cosmetic response: softness on SA 20 locks

|  | A | B | C | D | E | F |
|---|---|---|---|---|---|---|
| Softness | 3.00 | 3.25 | 4.00 | 3.50 | 4.25 | 3.00 |

Compositions C and E are markedly superior to A. Compositions D and F are equivalent to B.

The use of polymers such as Acrysol 22 in accordance with the invention make it possible to obtain gels of high viscosity and which are clear. By combining with the silicones defined in the invention, a synergy of viscosity is obtained which does not occur with Natrosol Plus. These silicones lead to a cosmetic improvement which does not occur with Natrosol Plus. The compositions in accordance with the invention therefore possess improved viscosity, clarity and cosmetic effect compared with the compositions of the prior art.

What is claimed is:

1. A composition comprising, in an aqueous phase, at least one amphiphilic polymer comprising at least one fatty chain and hydrophilic units, provided that said amphiphilic polymer is not a cellulose ether which has been made hydrophobic, and at least one polyoxyalkylenated silicone chosen from compounds of formulae (I), (II), (III), (IV) and (V):

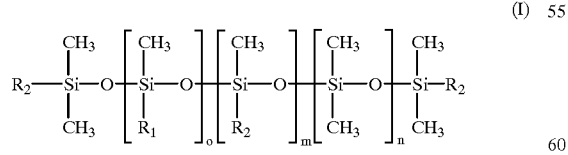

(I)

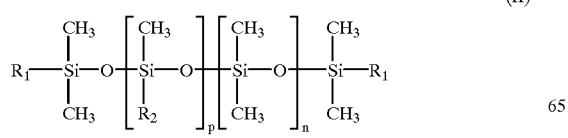

(II)

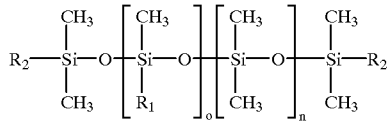

(III)

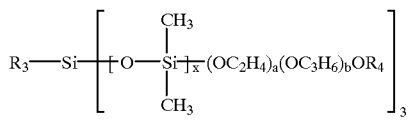

(IV)

$((Z(R_2SiO)_qR'_2SiZO)((C_nH_{2n}O)_r))_s$ (V)

wherein, in formulae (I), (II), (III) and (IV), $R_1$, which is identical or different, is chosen from linear and branched $C_1$–$C_{30}$ alkyl radicals and phenyl radicals, $R_2$, which is identical or different, is chosen from $-C_cH_{2c}-O-(C_2H_4O)_a(C_3H_6O)_b-R_5$ radicals and $-C_cH_{2c}-O-(C_4H_8O)_a-R_5$ radicals, $R_3$ and $R_4$, which are identical or different, are chosen from linear and branched $C_1$–$C_{12}$ alkyl radicals, $R_5$, which is identical or different, is chosen from a hydrogen atom, linear and branched alkyl radicals having 1 to 12 carbon atoms, linear and branched alkoxy radicals having 1 to 6 carbon atoms, linear and branched acyl radicals having 2 to 30 carbon atoms, $-SC_3M$ radicals, $C_1$–$C_6$ aminoalkoxy radicals optionally substituted on the amine, $C_2$–$C_6$ aminoacyl radicals optionally $-N(CH_2CH_2COOM)_2$ radicals, aminoalkyl radicals optionally substituted on the amine and on the alkyl chain, $C_2$–$C_{30}$ carboxyacyl radicals, phosphono groups optionally substituted with one or two substituted aminoalkyl radicals, $-CO(CH_2)_d COOM$ radicals, $-COCHR_7(CH_2)_d COOM$ radicals, $-NHCO(CH_2)_d OH$ radicals, $-NH_3Y$ radicals, and a phosphate group, M, which is identical or different, is chosen from a hydrogen atom, Na, K, Li, $NH_4$, and organic amines, $R_7$ is chosen from a hydrogen atom and $SO_3M$ radicals, d ranges from 1 to 10, m ranges from 0 to 20, n ranges from 0 to 500, o ranges from 0 to 20, p ranges from 1 to 50, a ranges from 0 to 50, b ranges from 0 to 50, a+b is greater than or equal to 2, c ranges from 0 to 4, x ranges from 1 to 100, Y is chosen from monovalent inorganic and organic anions, provided that when said silicone is chosen from compounds of formula (II) where $R_5$ is hydrogen, then n is greater than 12;

and wherein, in the formula (V):

R and R', which are identical or different, are chosen from monovalent hydrocarbon radicals, n ranges from 2 to 4, q is greater than or equal to 4, r is greater than or equal to 4, s is greater than or equal to 4, and Z is chosen from divalent organic groups which are linked to the adjacent silicon atom by a carbon-silicon bond and to a polyoxyalkylene block by an oxygen atom.

2. A composition according to claim 1, wherein said at least one amphiphilic polymer is chosen from optionally modified natural polymers, free-radical amphiphilic polymers, and polycondensates.

3. A composition according to claim 1, wherein said at least one amphiphilic polymer is chosen from anionic polymers and nonionic polymers.

4. A composition according to claim 1, wherein said composition further comprises less than 5% by weight of a surfactant relative to the total weight of said composition.

5. A composition according to claim 1, wherein said at least one amphiphilic polymer is present in an amount of from 0.1 to 15% by weight relative to the total weight of said composition.

6. A composition according to claim 5, wherein said at least one amphiphilic polymer is present in an amount of from 0.2 to 10% by weight relative to the total weight of said composition.

7. A composition according to claim 1, wherein said at least one polyoxyalkylenated silicone is present in an amount of from 0.005% to 15% by weight relative to the total weight of the composition.

8. A composition according to claim 1, wherein said at least one polyoxyalkylenated silicone and said at least one amphiphilic polymer are present in said composition in a weight ratio ranging from 0.1:1 to 10:1.

9. A composition according to claim 1, wherein said composition has a viscosity ranging from 200 to 30,000 cp.

10. A composition according to claim 1, wherein said composition is in the form of an aqueous gel or an emulsion.

11. A composition according to claim 1, wherein at least one of $R_3$ and $R_4$ is methyl.

12. A composition according to claim 1, wherein q ranges from 4 to 200, r ranges from 4 to 200, and s ranges from 4 to 1,000.

13. A composition according to claim 12, wherein q ranges from 4 to 100, r ranges from 5 to 100, and s ranges from 5 to 300.

14. A thickening agent for a composition comprising an aqueous phase, said thickening agent comprising, at least one amphiphilic polymer comprising at least one fatty chain and hydrophilic units, provided that said at least one amphiphilic polymer is not a cellulose ether which has been made hydrophobic, and at least one polyoxyalkylenated silicone chosen from compounds of formulae (I), (II), (Ill), (IV) and (V):

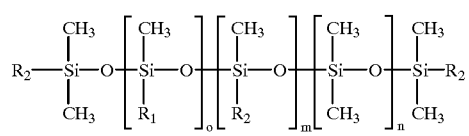

(I)

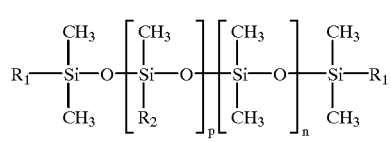

(II)

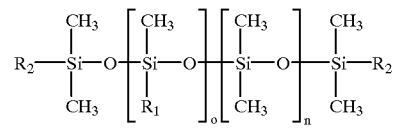

(III)

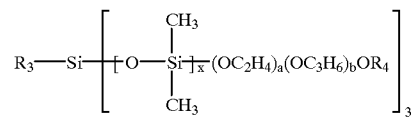

(IV)

(V)

wherein, in formulae (I), (II), (Ill) and (IV), $R_1$, which is identical or different, is chosen from linear and branched $C_1$–$C_{30}$ alkyl radicals and phenyl radicals, $R_2$, which is identical or different, is chosen from $-C_cH_{2c}-O-(C_2H_4O)_a(C_3H_6O)_b-R_5$ radicals and $-C_cH_{2c}-O-(C_4H_8O)_a-R_5$ radicals, $R_3$ and $R_4$, which are identical or different, are chosen from linear and branched $C_1$–$C_{12}$ alkyl radicals, $R_5$, which is identical or different, is chosen from a hydrogen atom, linear and branched alkyl radicals having 1 to 12 carbon atoms, linear and branched alkoxy radicals having 1 to 6 carbon atoms, linear and branched acyl radicals having 2 to 30 carbon atoms, $-SO_3M$ radicals, $C_1$–$C_6$ aminoalkoxy radicals optionally substituted on the amine, $C_2$–$C_6$ aminoacyl radicals optionally substituted on the amine, $-NHCH_2CH_2COOM$ radicals, $-N(CH_2CH_2COOM)_2$ radicals, aminoalkyl radicals optionally substituted on the amine and on the alkyl chain, $C_2$–$C_{30}$ carboxyacyl radicals, phosphono groups optionally substituted with one or two substituted aminoalkyl radicals, $-CO(CH_2)_dCOOM$ radicals, $-COCHR_7(CH_2)_dCOOM$ radicals, $-NHCO(CH_2)_dOH$ radicals, $-NH_3Y$ radicals, and a phosphate group, M, which is identical or different, is chosen from a hydrogen atom, Na, K, Li, $NH_4$, and organic amines, $R_7$ is chosen from hydrogen and $SO_3M$ radicals, d ranges from 1 to 10, m ranges from 0 to 20, n ranges from 0 to 500, o ranges from 0 to 20, p ranges from 1 to 50, a ranges from 0 to 50, b ranges from 0 to 50, a+b is greater than or equal to 2, c ranges from 0 to 4, x ranges from 1 to 100, Y is chosen from monovalent inorganic and organic anions, provided that when said silicone is chosen from compounds of formula (II) where $R_5$ is hydrogen, then n is greater than 12;

and wherein, in the formula (V):

R and R', which are identical or different, are chosen from monovalent hydrocarbon radicals, n ranges from 2 to 4, q is greater than or equal to 4,
r is greater than or equal to 4,
s is greater than or equal to 4, and
Z is chosen from divalent organic groups which are linked to the adjacent silicon atom by a carbon-silicon bond and to a polyoxyalkylene block by an oxygen atom.

15. A process for enhancing the thickening power of at least one amphiphilic polymer comprising at least one fatty chain and hydrophilic units, wherein said at least one amphiphilic polymer is not a cellulose ether that has been made hydrophobic and wherein said at least one amphiphilic polymer is present in a composition comprising an aqueous phase, said process comprising, adding to said composition at least one polyoxyalkylenated silicone chosen from compounds of formulae (I), (II), (III), (IV) and (V):

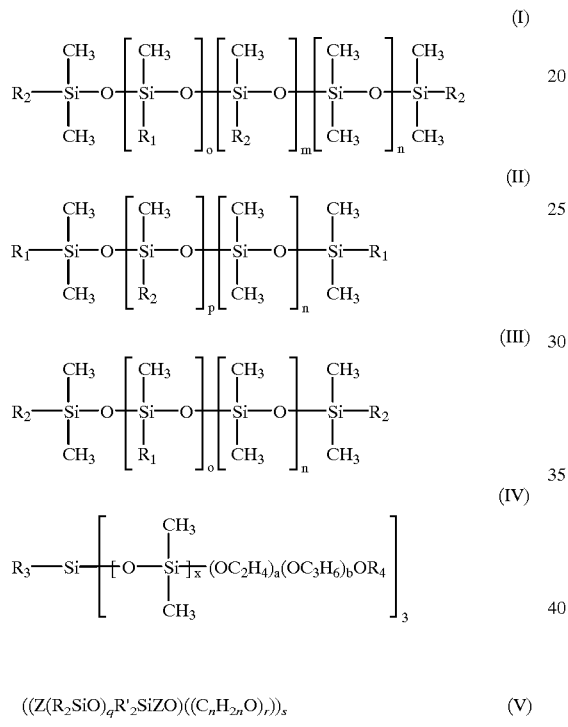

$$((Z(R_2SiO)_q R'_2 SiZO)((C_n H_{2n} O)_r))_s \qquad (V)$$

wherein, in formulae (I), (II), (III) and (IV), $R_1$, which is identical or different, is chosen from linear and branched $C_1-C_{30}$ $R_2$, which is identical or different, is chosen from —$C_cH_{2c}$—O—$(C_2H_4O)_a(C_3H_6O)_b$—$R_5$ radicals and —$C_cH_{2c}$—O—$(C_4H_8O)_a$—$R_5$ radicals, $R_3$ and $R_4$, which are identical or different, are chosen from linear and branched $C_1-C_{12}$ alkyl radicals, $R_5$, which is identical or different, is chosen from a hydrogen atom, linear and branched alkyl radicals having 1 to 12 carbon atoms, linear and branched alkoxy radicals having 1 to 6 carbon atoms, linear and branched acyl radicals having 2 to 30 carbon atoms, —$SO_3M$ radicals, $C_1-C_6$ aminoalkoxy radicals optionally substituted on the amine, $C_2-C_6$ aminoacyl radicals optionally substituted on the amine, —$NHCH_2CH_2COOM$ radicals, —$N(CH_2CH_2COOM)_2$ radicals, aminoalkyl radicals optionally substituted on the amine and on the alkyl chain, $C_2-C_{30}$ carboxyacyl radicals, phosphono groups optionally substituted with one or two substituted aminoalkyl radicals, —$CO(CH_2)_dCOOM$ radicals, —$COCHR_7(CH_2)_dCOOM$ radicals, —$NHCO(CH_2)_dOH$ radicals, —$NH_3Y$ radicals, and a phosphate group, M, which is identical or different, is chosen from hydrogen, Na, K, Li, $NH_4$, and organic amines, $R_7$ is chosen from hydrogen and $SO_3M$ radicals, d ranges from 1 to 10, m ranges from 0 to 20, n ranges from 0 to 500, o ranges from 0 to 20, p ranges from 1 to 50, a ranges from 0 to 50, b ranges from 0 to 50, a+b is greater than or equal to 2, c ranges from 0 to 4, x ranges from 1 to 100, Y is chosen from monovalent inorganic and organic anions, provided that when said silicone is chosen from compounds of formula (II) where $R_5$ is hydrogen then n is greater than 12;

and wherein, in the formula (V)

R and R', which are identical or different, are chosen from monovalent hydrocarbon radicals, n ranges from 2 to 4, q is greater than or equal to 4, r is greater than or equal to 4, s is greater than or equal to 4, Z is chosen from divalent organic groups which are linked to the adjacent silicon atom by a carbon-silicon bond and to a polyoxyalkylene block by an oxygen atom.

* * * * *

UNITED STATES PATENT AND TRADEMARK OFFICE
CERTIFICATE OF CORRECTION

PATENT NO. : 6,369,117 B1
DATED : April 9, 2002
INVENTOR(S) : Dubief et al.

It is certified that error appears in the above-identified patent and that said Letters Patent is hereby corrected as shown below:

<u>Column 11,</u>
Line 52, "(Ill)" should read -- III --.

<u>Column 12,</u>
Line 32, "-SC$_3$M" should read -- SO$_3$M --.
Line 34, after "optionally", insert -- substituted on the amine, -NHCH$_2$CH$_2$COOM radicals, and --.

<u>Column 13,</u>
Line 52, "(Ill)" should read -- III --.

<u>Column 14,</u>
Line 18, "(Ill)" should read -- III --.

<u>Column 15,</u>
Line 16, "(Ill)" should read -- III --.
Line 45, "(Ill)" should read -- III --.
Line 47, after "C$_1$-C$_{30}$", insert -- alkyl radicals and phenyl radicals, --.

Signed and Sealed this

Seventeenth Day of September, 2002

*Attest:*

*Attesting Officer*

JAMES E. ROGAN
*Director of the United States Patent and Trademark Office*